United States Patent [19]

Felstead et al.

[11] 4,368,042

[45] Jan. 11, 1983

[54] DEVICE FOR USE IN MAKING A DENTAL REPLICA, AND A METHOD OF MAKING A DENTAL REPLICA

[76] Inventors: John T. Felstead, 86 Collins Meadow, Harlow, Essex; John C. Gerrard, 5, The Oval, Broxbourne, Hertfordshire, both of England

[21] Appl. No.: 283,038

[22] Filed: Jul. 13, 1981

[30] Foreign Application Priority Data

Jul. 11, 1980 [GB] United Kingdom ............... 8022692
Nov. 7, 1980 [GB] United Kingdom ............... 8035822

[51] Int. Cl.³ .......................................... A61C 11/00
[52] U.S. Cl. .................................................. 433/213
[58] Field of Search ......................... 433/213, 54, 74

[56] References Cited

U.S. PATENT DOCUMENTS 2,700,218  1/1955  Lindley ............................ 433/213
4,265,619  5/1981  Lucki et al. ..................... 433/213

Primary Examiner—Robert Peshock
Attorney, Agent, or Firm—Leydig, Voit, Osann, Mayer and Holt, Ltd.

[57] ABSTRACT

A device for use in making a dental replica comprises a jaw-shaped plate having on both surfaces thereof a pattern of parallel zigzag ribs and grooves, and a base having on the upper surface thereof a complementary pattern of parallel zigzag ribs and grooves capable of interlocking with the pattern on the plate. There is also disclosed a method of making a dental replica utilizing such a device wherein the replica may be separated into pieces each having a portion of the plate keyed thereto and the separated pieces reassembled on the base.

5 Claims, 3 Drawing Figures

DEVICE FOR USE IN MAKING A DENTAL REPLICA, AND A METHOD OF MAKING A DENTAL REPLICA

This invention relates to a device for use in making a dental replica, and to a method of making a dental replica.

When a tooth is to be crowned or otherwise rebuilt, it is conventional to take an impression of the tooth using a rubber-like impression material, which is used as a mould from which to prepare a replica tooth. The replica may then be used to build up a model of the crowned tooth which serves as a pattern for making the crown. Often a replica of one or both sets of teeth will be prepared so that it is possible to see what the finished tooth will look like in situ, and to ensure that the top and bottom set will still close together properly.

However, when working on the individual replica tooth it is convenient to remove it from the set. To do this the jaw-shaped replica of the gum and set of teeth is cut through and a slice of replica gum and its tooth removed from the set.

In order to provide a template on which to reassemble the pieces of the set, a removable base is cast onto the replica before it is cut up. So that the individual pieces may be accurately reassembled each one is provided with a locating pin which fits into a hole in the base. The pins are set into the replica at the time of moulding it.

However, this technique for reassembling the pieces of the replica suffers from a number of disadvantages. The first disadvantage is that it is necessary to accurately locate the pin into the piece of replica carrying the tooth in question prior to setting. This is not easily done when the impression is full of moulding material, since the outline of the teeth is not visible from the outside of the impression. Also, if a pin is forgotten it cannot be set in later.

The second disadvantage is that the base must be removably moulded onto the replica. This is time-consuming and wasteful since the base is individual to the replica in question and cannot be reused.

A further disadvantage is that the pins do not locate the pieces very precisely on the base, particularly as the pieces become worn. Thus, it is normal to saw only part-way through the replica and then to break the piece off, so as to avoid forming a slot between adjacent pieces which would allow a certain degree of movement.

The present invention aims to overcome the disadvantages of the prior art.

The present invention in one aspect provides a device for use in making a dental replica, comprising a plate which is generally jaw-shaped and which has on at least one surface thereof a pattern which comprises a series of parallel zigzag ribs and grooves, and a base having on the upper surface thereof a complementary pattern which comprises a series of parallel zigzag ribs and grooves capable of interlocking with the said pattern on the plate.

The plate preferably has on both surfaces thereof identical patterns each comprising a series of parallel zigzag ribs and grooves. This provides a plate of symmetrical construction, giving practical advantages which will be fully described subsequently.

The invention in another aspect provides a method of making a dental replica, comprising filling a dental impression with moulding material; embedding in the moulding material one surface of a plate having thereon means for keying the plate into the moulding material, the plate having on the other surface thereof a pattern which comprises a series of parallel zigzag ribs and grooves; allowing the moulding material to set; removing the set replica from the impression; separating the replica into pieces comprising teeth or groups of teeth, each having a portion of the plate keyed thereto; and reassembling the separated pieces on a base having on the upper surface thereof a complementary pattern which comprises a series of parallel zigzag ribs and grooves which interlock with the said pattern on the plate.

The means on the one surface of the plate for keying the plate into the moulding material is preferably a pattern comprising a series of parallel zigzag ribs and grooves identical to the pattern on the other surface of the plate, thus providing a plate of symmetrical construction as described above.

The invention will be further described, by way of example only, with reference to the accompanying drawings, in which.

Figure 1:
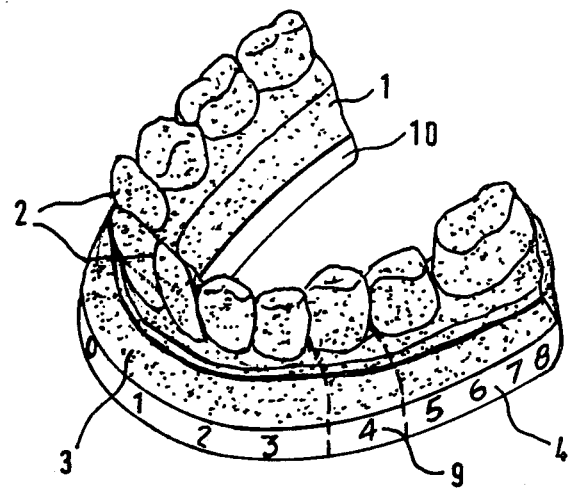
FIG. 1 is a perspective view of a dental replica mounted on a plate, and a base for receiving the plate.
Figure 1:
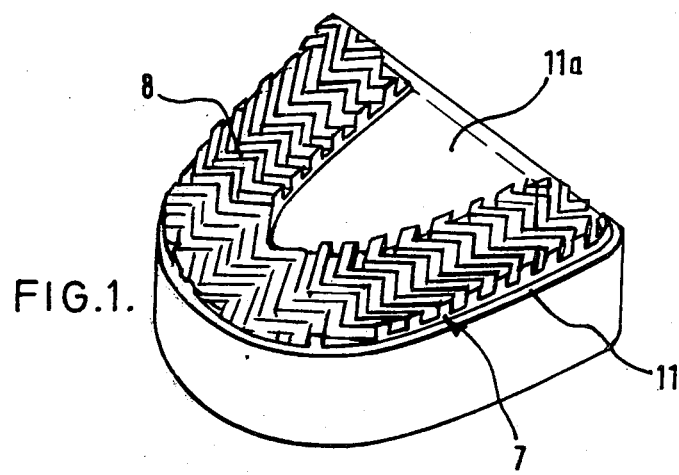

FIG. 1 shows a dental replica 1 comprising teeth 2 and gums 3 mounted on a plate 4, and a base 7 for supporting the plate. As can be seen more clearly from FIGS. 2 and 3 the plate 4 is generally jaw-shaped and has on both surfaces thereof identical patterns each comprising a series of parallel zigzag ribs 5 and grooves 6. The upper surface of the base 7 has thereon a pattern 8 which complements the pattern on the plate 4 and comprises a series of parallel zigzag ribs and grooves capable of firmly interlocking with the pattern on the plate.

The zigzag pattern on the upper surface of the plate 4 keys the dental replica 1 onto the plate. The pattern on the lower surface enables the plate to be locked onto the base 7, which carries a complementary pattern. Because of the continuous nature of the pattern, small pieces comprising a tooth or group of teeth, e.g. piece 9 shown dotted, cut from the replica through the plate 4 will each include a small portion of the plate 4. Despite its small size the piece 9 carries enough of the pattern 5,6 to ensure positive relocation of the piece in its predetermined correct position when the replica pieces are reassembled on the base 7. Because the pattern 5,6 has a large repeating unit (for example the longest rib 5 shown in FIG. 2 comprises five repeating units only) relative to the size of the plate 4, the risk of reassembling replica pieces in incorrect positions is small. A replica piece would have to be displaced one whole repeating unit sideways or downwards from its correct position before it could again be locked on the base.

A lip 10 for assisting location of the plate 4 on the base 7 extends around the entire periphery of the plate and projects from both surfaces thereof. The upper part of the base carrying the pattern thereon is also made jaw-shaped corresponding to the shape of the plate and has extending around the edge thereof a ledge 11 for receiving the lip 10. The ledge 11 is supplemented by a cut-out part 11a as shown so that the whole of the lip 10 is suitably supported.

In order to make the plate 4 symmetrical with respect to the centre line 3—3, the lip 10 and pattern 5,6 are symmetrically disposed on both the upper and lower faces of plate 4. The plate 4 is symmetrical to 180° rotation about the axis defined by centre-line 3—3. This arrangement is convenient in that it allows the plate 4 to be cut along centre-line 3—3 into two identical non-handed halves. If it is only necessary to make a replica of the teeth on one side of the mouth only half of the plate is used. The remaining half may however still be used for either the left or right side of the mouth. If the plate is not symmetrical, there is a possibility that an operator might be left with a wasteful surfeit of halves of a particular hand. The pattern 5,6 is thus also symmetrical.

Both the plate 4 and the base 7 are moulded of a plastics material, e.g. a polyacrylate.

The base 7 is suitably hollow, the bottom thereof being closable by a press-fitted lid, so that the base may be used to contain dental replica work. The function of the base as a container in which such dental work may be stored or transported allows the device according to the invention comprising the plate and base to be used as a complete unit for carrying out dental replica work.

Operation is as follows. A dental impression of a patient's set of teeth is taken by biting into curable rubber-like impression material loaded into a jaw-shaped trough in conventional manner. The impression is then filled with a hard cement-like dental moulding material and a plate 4 is pressed into the surface of the moulding material before it sets. The ribs 5 and grooves 6 become embedded into the moulding material, which is then allowed to set.

The hardened replica 1 is removed from the impression and a tooth selected for treatment, e.g. the building up of a crown, removed from the replica by cutting along the dotted lines (FIG. 1) to separate a piece 9. The two remaining pieces of the replica are locked onto the base in their correct positions. As work on the tooth of removed piece 9 progresses, the piece is periodically replaced in position on the base 7 to check its visual harmony with the other teeth. If it is necessary to check the alignment of the top set of teeth with the bottom set, the base 7 and assembled teeth are loaded into an appropriate hinged device simulating jaw movement, known as an articulator. Because they are locked onto the base the individual replica pieces do not fall off on inversion.

Figure 2:
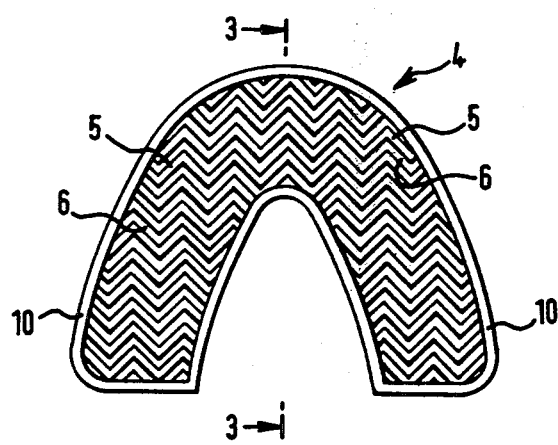
FIG. 2 is a view of the plate from above.
Figure 3:
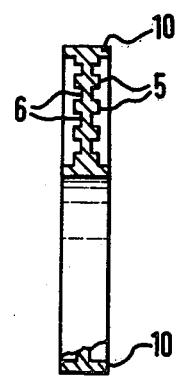
FIG. 3 is a cross-sectional view taken along the line 3—3 in FIG. 2.

As shown in FIGS. 1 and 2, the edge of the plate 4 carries along each side a series of numbers 1 to 8 approximately corresponding to the position of the individual teeth. The front centre position is marked with a zero. The base 7 carries a corresponding series of numbers to facilitate relocation of the replica pieces on the base. The zero allows the two front teeth "1" to be distinguished from each other.

It has been found that the pattern of parallel zigzag ribs and grooves employed provides precise location between the plate 4 and the base 7, even when a piece 9 carried by a corresponding portion of plate 4 is very small. Other manners of locking between the plate and base have been investigated by the inventors but have been found to be unsatisfactory in practice. For example providing a series of stud-like projections on the lower surface of the plate and corresponding holes for receiving the projections in the upper surface of the base 7 gives a connection which, while to some extent satisfactory for large pieces 9, is unsatisfactory for small pieces 9 because of the necessity of having to cut through the stud-like projections when cutting the plate. The pattern of zigzag ribs and grooves described above has been found to be far superior in practice.

We claim:

1. A device for use in making a dental replica, comprising a plate which is generally jaw-shaped and which has on at least one surface thereof a pattern which comprises a series of parallel zigzag ribs and grooves, said plate having means on one surface for receiving a molded dental replica and being adapted to be separated into individual tooth pieces, and a base having on the upper surface thereof a complementary pattern which comprises a series of parallel zigzag ribs and grooves capable of interlocking with said pattern on the plate to secure said plate or said individual tooth pieces on said base in predetermined locations.

2. The device according to claim 1, wherein the plate has on both surfaces thereof identical patterns each comprising a series of parallel zigzag ribs and grooves, said pattern on one surface providing said means for receiving a molded dental replica and keying the same to said plate, said pattern on the other surface interlocking with said complementary pattern on said base.

3. The device according to claim 1, wherein a lip extends around the edge of the plate for assisting location of the plate on a ledge formed on the upper surface of the base.

4. A method of making a dental replica, comprising filling a dental impression with moulding material; embedding in the moulding material one surface of a plate having thereon means for keying the plate into the moulding material, the plate having on the other surface thereof a pattern which comprises a series of parallel zigzag ribs and grooves; allowing the moulding material to set; removing the set replica from the impression; separating the replica into pieces each comprising at least one tooth, each piece having a portion of the plate keyed thereto; and reassembling the separated pieces on a base having on the upper surface thereof a complementary pattern which comprises a series of parallel zigzag ribs and grooves which interlock with said pattern on the plate.

5. The method according to claim 4, wherein said means on said one surface of the plate for keying the plate into the moulding material is a pattern comprising a series of parallel zigzag ribs and grooves identical to said pattern on said other surface of the plate.

* * * * *